United States Patent [19]

Majeti et al.

[11] Patent Number: 5,281,411

[45] Date of Patent: Jan. 25, 1994

[54] ORAL COMPOSITIONS

[75] Inventors: Satyanarayana Majeti; Christopher B. Guay; Mark M. Crisanti, all of Cincinnati, Ohio

[73] Assignee: The Procter & Gamble Company, Cincinnati, Ohio

[21] Appl. No.: 923,037

[22] Filed: Jul. 31, 1992

[51] Int. Cl.$^5$ ............................ A61K 7/16; A61K 7/18
[52] U.S. Cl. ......................................... 424/52; 424/49
[58] Field of Search ....................... 424/49–58

[56] References Cited

U.S. PATENT DOCUMENTS

| | | |
|---|---|---|
| 2,839,448 | 6/1958 | Hager et al. . |
| 2,946,725 | 7/1960 | Norris et al. . |
| 3,105,798 | 10/1963 | Holliday et al. ............... 424/52 |
| 3,282,792 | 11/1966 | Fiscella . |
| 3,934,002 | 1/1976 | Haefele . |
| 3,937,806 | 2/1976 | Cooley ............................ 424/52 |
| 3,939,262 | 2/1976 | Kim . |
| 3,957,968 | 5/1976 | Cordon . |
| 4,007,260 | 2/1977 | Kim ................................ 424/52 |
| 4,011,309 | 3/1977 | Lutz . |
| 4,256,731 | 3/1981 | Curtis et al. . |
| 4,323,551 | 4/1982 | Parran, Jr. . |
| 4,335,102 | 6/1982 | Nakashima et al. . |
| 4,363,794 | 12/1982 | Ochiai et al. . |
| 4,522,806 | 6/1985 | Muhlemann et al. . |
| 4,568,540 | 2/1986 | Asano ............................. 424/52 |
| 4,592,487 | 6/1986 | Simon et al. . |
| 4,702,904 | 10/1987 | Maeyama et al. . |
| 4,822,599 | 4/1989 | Mitra . |
| 4,925,655 | 5/1990 | Smigel et al. . |
| 4,986,981 | 1/1991 | Glace et al. . |
| 5,004,597 | 4/1991 | Majeti et al. ................... 424/52 |
| 5,094,842 | 3/1992 | Riley . |
| 5,145,666 | 9/1992 | Lukacovic et al. ............ 424/52 |

FOREIGN PATENT DOCUMENTS

| | | |
|---|---|---|
| 0287590 | 3/1965 | Australia . |
| 0311259 | 4/1989 | European Pat. Off. . |
| 0311260 | 4/1989 | European Pat. Off. . |
| 0422803 | 4/1991 | European Pat. Off. . |
| 0427175 | 5/1991 | European Pat. Off. . |
| 976742 | 12/1964 | United Kingdom . |
| 1018665 | 1/1966 | United Kingdom . |
| 1032618 | 6/1966 | United Kingdom . |
| 1066466 | 4/1967 | United Kingdom . |

*Primary Examiner*—Shep K. Rose
*Attorney, Agent, or Firm*—D. C. Mohl; D. K. Dabbiere; J. C. Rasser

[57] ABSTRACT

Oral compositions possessing antiplaque and antigingivitis properties containing stannous gluconate are described herein.

8 Claims, No Drawings

ORAL COMPOSITIONS

TECHNICAL FIELD

The present invention relates to oral compositions such as liquid dentifrices, toothpastes, mouthwashes, chewing gum, tablets and powders which provide antiplaque and antigingivitis benefits.

BACKGROUND OF THE INVENTION

Plaque is recognized as a precursor of such oral diseases as caries and gingivitis. The gums of the mouth of humans and lower animals may be harmed by deposits of dental plaque, a combination of minerals and bacteria found in the mouth. The bacteria associated with plaque can secrete enzymes and endotoxins which can irritate the gums and cause an inflammatory gingivitis. As the gums become increasingly irritated by this process they have a tendency to bleed, lose their toughness and resiliency, and separate from the teeth, leaving periodontal pockets in which debris, secretions, more bacteria and toxins further accumulate. It is also possible for food to accumulate in these pockets, thereby providing nourishment for increased growth of bacteria and production of endotoxins and destructive enzymes. This can result in destruction of bone and gum tissue.

With such problems being possible from plaque/gingivitis it is not surprising that extensive efforts have been expended in trying to find effective treatment compositions. Many of these efforts have used quaternary ammonium compounds or bis-biquanides such as chlorhexidine which is used in Peridexo sold by The Procter & Gamble Company.

Another material which has been considered is stannous ion. Such a material is disclosed in Svatun B., "Plaque Inhibiting Effect of Dentifrices Containing Stannous Fluoride", *Acta Odontol. Scand.*, 36, 205-210 (1978); and Bay I., and Rolla, G., "Plaque Inhibition and Improved Gingival Condition by Use of a Stannous Fluoride Toothpaste", *Scand. J. Dent. Res.*, 88, 313-315 (1980). Additionally stannous fluoride stabilized with stannous gluconate has been used to treat plaque and gingivitis and disclosed in to Majeti et al. U.S. Pat. No. 5,004,597, Apr. 2, 1991.

In spite of the many disclosures in the antiplaque/antigingivitis area, the need for products still exists. The present invention is directed to the recognition that stannous gluconate when used without stannous fluoride, or with only very low levels of this material can provide plaque and gingivitis reductions.

It is an object of the present invention therefore to provide compositions which deliver an improved antiplaque/antigingivitis benefit.

It is a further object of the present invention to provide improved products utilizing stannous gluconate.

It is still a further object of the present invention to provide an effective method for treating plaque/gingivitis with the above described compositions.

These and other objects will become clearer from the detailed description which follows.

All percentages and ratios used herein are by weight of the total composition unless otherwise specified. Additionally, all measurements are made at 25° C. in the composition or in an aqueous solution/dispersion unless otherwise specified.

SUMMARY OF THE INVENTION

The present invention embraces an oral composition comprising:
a) a safe and effective amount of stannous gluconate; and
b) a pharmaceutically acceptable carrier
wherein said composition has a pH of from about 3.0 to about 5.0 and is substantially free of calcium ion sources and stannous fluoride. By "substantially free" is meant less than about 0.05% for stannous fluoride and less than about 2.0% for the other materials.

The present invention also encompasses a method for retarding the development of plaque/gingivitis using these compositions.

DETAILED DESCRIPTION OF THE INVENTION

The compositions of the present invention comprise stannous gluconate and a pharmaceutically acceptable carrier.

By "oral composition" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "safe and effective amount" as used herein means sufficient amount of material to provide the desired benefit while being safe to the hard and soft tissues of the oral cavity.

By the term "comprising", as used herein, is meant that various additional components can be conjointly employed in the compositions of this invention as long as the listed materials perform their intended functions.

By the term "carrier", as used herein, is meant a suitable vehicle which is pharmaceutically acceptable and can be used to apply the present compositions in the oral cavity.

Stannous Gluconate

Stannous gluconate is the essential component of the present compositions. This material is a known stannous chelate and may be provided to the present compositions as the chelate or as separate soluble stannous and gluconate salts and the chelate formed in-situ. Such salts include stannous chloride and sodium gluconate. Stannous gluconate is present in the present compositions at a level of from about 0.1% to about 11%, preferably from about 2% to about 4%.

Pharmaceutically Acceptable Carrier

The carrier for the stannous components can be any vehicle suitable for use in the oral cavity. Such carriers include the usual components of toothpastes, mouthwashes, tooth powders, prophylaxis pastes, lozenges, gums and the like and are more fully described hereinafter. Dentifrices and mouthwashes are the preferred systems.

The abrasive polishing material contemplated for use in the dentifrice aspect of the present invention can be any material which does not excessively abrade dentin. These include, for example, silicas including gels and precipitates, insoluble sodium polymetaphosphate, β-phase calcium pyrophosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. For these reasons they are preferred for use herein.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al. U.S. Pat. No. 3,538,230, issued Mar. 2, 1970 and Digiulio U.S. Pat. No. 3,862,307, Jun. 21, 1975, both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, Jul. 29, 1982, incorporated herein by reference.

The abrasive in the compositions described herein is present at a level of from about 6% to about 70%, preferably from about 15% to about 25% when the dentifrice is a toothpaste. Higher levels, as high as 95%, may be used if the composition is a toothpowder.

Flavoring agents can also be added to dentifrice compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Dentifrice compositions can also contain emulsifying agents. Suitable emulsifying agents are those which are reasonably stable and foam throughout a wide pH range, including non-soap anionic, nonionic, cationic, zwitterionic and amphoteric organic synthetic detergents. Many of these suitable surfactants are disclosed by Gieske et al. in U.S. Pat. No. 4,051,234, Sep. 27, 1977, incorporated herein by reference.

It is common to have a water-soluble fluoride compound present in dentifrices and other oral compositions in an amount sufficient to give a fluoride ion concentration in the compositions at 25° C. and/or when it is used of from about 0.0025% to about 5.0% by weight, preferably from about 0.005% to about 2.0% by weight, to provide additional anticaries effectiveness. Preferred fluorides are sodium fluoride, indium fluoride, and sodium monofluorophosphate. Norris et al. U.S. Pat. No. 2,946,735, issued Jul. 26, 1960 to Widder et al., U.S. Pat. No. 3,678,154, issued Jul. 18, 1972 disclose such salts as well as others.

Water is also present in the toothpastes of this invention. Water employed in the preparation of commercially suitable toothpastes should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols at a total level of from about 15% to about 70%.

Also desirable for inclusion in the toothpastes of the present invention are other stannous salts such as stannous pyrophosphate and antimicrobials such as quaternary ammonium salts, bis-biquanide salts, nonionic antimicrobial salts and flavor oils. Such agents are disclosed in U.S. Pat. No. 2,946,735, Jul. 26, 1960, to Norris et al., U.S. Pat. No. 4,894,220, Jan. 16, 1990 to Nabi et al., and U.S. Pat. No. 4,051,234, Sep. 27, 1977 to Gieske et al., incorporated herein by reference. These agents, if present, are included at levels of from about 0.01% to about 1.5%.

Another preferred embodiment of the present invention is a mouthwash composition. Conventional mouthwash composition components can comprise the carrier for the antimicrobial of the present invention. Mouthwashes generally comprise from about 20:1 to about 2:1 of a water/ethyl alcohol solution and preferably other ingredients such as flavor, sweeteners, humectants and sudsing agents such as those mentioned above for dentifrices. The humectants, such as glycerin and sorbitol give a moist feel to the mouth. Generally, on a weight basis the mouthwashes of the invention comprise 5% to 60% (preferably 18% to 25%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to 0.3% (preferably 0.03% to 0.3%) flavoring agent, and the balance water. The amount of additional antimicrobial agent in mouthwashes is typically from about 0.01% to about 1.5% by weight. Mouthwash type products may also be formed by dissolving a powder or tablet containing stannous gluconate in water just prior to use.

Suitable lozenge and chewing gum components are disclosed in U.S. Pat. No. 4,083,955, Apr. 11, 1978 to Grabenstetter et al., incorporated herein by reference.

The pH of the present compositions and/or its pH in the mouth can be any pH which is safe for the mouth's hard and soft tissues and will provide optimal effect of the stannous gluconate. Such pH's are from about 3.0 to about 5.0, preferably from about 4.0 to about 5.0, most preferably about 4.5.

The present compositions may cause some staining of hard surfaces in the mouth. Such staining may be reduced or eliminated by using a composition containing pyrophosphate ions and/or citric ions as disclosed in copending application 781,443, filed Oct. 23, 1991, incorporated herein by reference.

METHOD OF MANUFACTURE

The carrier compositions of the present invention can be made using methods which are common in the oral products area. A specific method of manufacture is set forth in the Examples.

COMPOSITION USE

The present invention in its method aspect involves applying to the oral cavity safe and effective amounts of the compositions described herein. These amounts (e.g. from about 0.3 to about 15 g), if it is a toothpaste or mouthwash, are kept in the mouth for from about 15 to about 60 seconds.

The following examples further describe and demonstrate preferred embodiments within the scope of the present invention. The examples are given solely for illustration and are not to be construed as limitations of this invention as many variations thereof are possible without departing from the spirit and scope thereof.

EXAMPLE I
Toothpaste

|  | Weight % | Weight % |
| --- | --- | --- |
| Water | 12.500 | 12.500 |
| Sorbitol | 45.425 | 44.552 |
| Glycerin | 10.198 | 10.198 |
| Titanium Dioxide | 0.525 | 0.525 |
| Silica | 20.000 | 20.000 |
| Na Carboxymethyl Cellulose | 1.050 | 1.050 |
| Magnesium Aluminum Silicate | 0.408 | 0.408 |
| Na Alkyl Sulfate (27.9% Solution) | 4.000 | 4.000 |
| Na Gluconate | 1.738 | 3.476 |
| Stannous Chloride Dihydrate | 1.794 | 1.794 |
| Na Saccharin | 0.200 | 0.200 |
| Flavor | 0.851 | 0.851 |
| FD&C Blue #1 (1% Solution) | 0.051 | 0.051 |
| Na Monofluoro Phosphate | 0.760 | — |
| Na Hydroxide (50% Solution) | 0.500 | 0.395 |
| pH | 4.5 | 4.5 |

EXAMPLE II
Mouthrinse

|  | Weight % | Weight % |
| --- | --- | --- |
| Stannous Chloride Dihydrate | 0.519 | 0.519 |
| Sodium Gluconate | 0.521 | 1.041 |
| Glycerin | 8.000 | 12.000 |
| Sorbitol (70% Aqueous Solution) | — | — |
| Ethanol | 10.000 | 10.000 |
| Polysorbate 80 | 0.300 | 0.300 |
| Sodium Saccharin | 0.050 | 0.050 |
| Flavor | 0.150 | 0.150 |
| Sodium Hydroxide | 0.020 | 0.020 |
| Benzoic Acid | 0.050 | 0.050 |
| FD&C Blue #1 (1% Solution) | 0.020 | 0.020 |
| Sodium Monofluoro Phosphate | 0.183 | — |
| Water pH | 80.187 | 77.850 |

EXAMPLE III
Topical Gel

|  | Weight % | Weight % |
| --- | --- | --- |
| Stannous Chloride Dihydrate | 1.794 | 2.153 |
| Sodium Gluconate | 1.750 | 2.082 |
| Glycerin | 91.896 | 70.000 |
| Sorbitol (70% Solution) | — | 21.765 |
| Sodium Carboxymethyl Cellulose | 0.600 | 0.800 |
| Hydroxyethyl Cellulose | — | — |
| Flavor | 1.000 | 1.000 |
| Sodium Saccharin | 0.200 | 0.200 |
| Sodium Alkyl Sulfate (27.9%) | 2.000 | 2.000 |
| Sodium Monofluoro Phosphate | 0.760 | — |

EXAMPLE IV
Mouthrinse Tablet

|  | Weight % | Weight % |
| --- | --- | --- |
| Stannous Chloride Dihydrate | 0.519 g | 0.519 g |
| Sodium Gluconate | 0.500 g | 0.700 g |
| Flavor | 0.150 g | 0.150 g |
| Sodium Saccharin | 0.050 g | 0.200 g |
| Mannitol | 0.773 g | — |
| Sodium Carboxymethyl Cellulose | 0.050 g | — |
| Sodium Benzoate | 0.030 g | 0.025 g |
| Citric Acid | — | 0.200 g |
| Sodium Carbonate | — | 0.100 g |
| Sodium Bicarbonate | — | 0.200 g |
| Glycine | — | 0.050 g |
| Sodium Monofluoro Phosphate | 0.183 g | — |
|  | 2.255 g | 2.144 g |
|  | Dissolve in 97.745 g water | Dissolve in 97.856 g water |

What is claimed is:

1. An oral composition effective in treating plaque/gingivitis consisting essentially of:
   (a) a safe and effective amount of stannous gluconate; and
   (b) a pharmaceutically acceptable fluoride toothpaste carrier wherein the pH of said composition is from about 3.0 to about 5.0 and said composition contains less than about 2.0% of a calcium ion source(s) and less than about 0.05% stannous fluoride.

2. An oral composition according to claim 1 wherein the amount of stannous gluconate is from about 0.1% to about 11%.

3. An oral composition according to claim 2 wherein the pharmaceutically acceptable carrier is a toothpaste which also contains an effective amount of sodium monofluorophosphate.

4. An oral composition according to claim 3 which also contains a silica dental abrasive.

5. An oral composition according to claim 4 which also contains another stannous salt, other than stannous fluoride.

6. A method of reducing gingivitis by applying to the oral cavity a safe and effective amount of a composition according to claim 1.

7. A method according to claim 6 wherein the composition is according to claim 3.

8. A method according to claim 6 wherein following the use of a composition according to claim 1 is used a composition containing pyrophosphate and/or citrate ions to reduce stain.

* * * * *